(12) United States Patent
Baumgartner et al.

(10) Patent No.: US 6,855,253 B2
(45) Date of Patent: Feb. 15, 2005

(54) ANAEROBIC DIGESTER

(75) Inventors: John W. Baumgartner, Olivia, MN (US); Mark K. Kubesh, Olivia, MN (US); Wade E. Jager, Eddyville, IA (US)

(73) Assignee: Baumgartner Environics, Inc., Olivia, MN (US)

( * ) Notice: Subject to any disclaimer, the term of this patent is extended or adjusted under 35 U.S.C. 154(b) by 0 days.

(21) Appl. No.: 10/668,636

(22) Filed: Sep. 22, 2003

(65) Prior Publication Data

US 2004/0055952 A1 Mar. 25, 2004

Related U.S. Application Data

(60) Provisional application No. 60/413,068, filed on Sep. 23, 2002.

(51) Int. Cl.$^7$ .................................................. C02F 3/28
(52) U.S. Cl. ...................................... 210/603; 210/615
(58) Field of Search ............................ 210/603, 188, 210/615; 435/289.1; 71/10

(56) References Cited

U.S. PATENT DOCUMENTS

| | | | |
|---|---|---|---|
| 3,933,628 A | | 1/1976 | Varani |
| 4,092,338 A | * | 5/1978 | Tossey ........................ 210/142 |
| 4,201,663 A | | 5/1980 | Rollag et al. |
| 4,579,654 A | * | 4/1986 | Bremmer ..................... 210/180 |
| 5,562,759 A | | 10/1996 | Morgan et al. |
| 6,361,249 B1 | | 3/2002 | Hodgkinson et al. |
| 6,451,206 B1 | * | 9/2002 | Charbonneau .............. 210/170 |

FOREIGN PATENT DOCUMENTS

JP         61-178016     * 8/1996

* cited by examiner

*Primary Examiner*—Fred G. Prince
(74) *Attorney, Agent, or Firm*—Gray, Plant, Mooty, Mooty and Bennett, P.A.; Robert W. Gutenkauf

(57) ABSTRACT

An anaerobic digester and a method for treating organic waste and recovering a usable quality methane gas. A first cover of gas permeable material conducive to bacterial colonization covers the surface of a slurry of organic waste material in a containment vessel. The permeable cover acts as a media to support and encourage the growth of methanogenic bacteria. Gas collection apparatus is installed on the first cover. A second cover of gas impermeable material is installed over the gas collection apparatus. A gas collection space is formed between the two covers. Edges of the first and second covers are closed to inhibit the escape of gas from the gas collection space. Biogas produced as a result of anaerobic digestion activity permeates the gas permeable cover and enters the collection space. From the collection space the gas is drawn into the gas collection apparatus which can, for example, be comprised of a network of perforated ducts connected to a blower that draws gas out of the ducts for delivery to a storage or usage location.

28 Claims, 2 Drawing Sheets

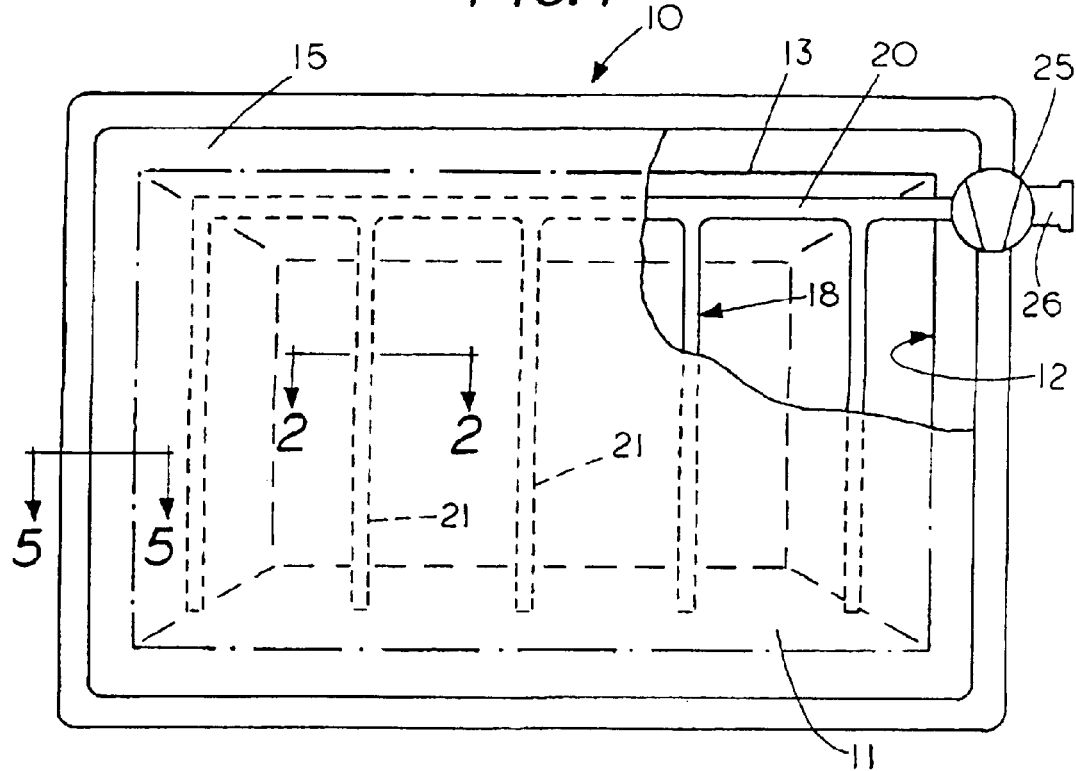
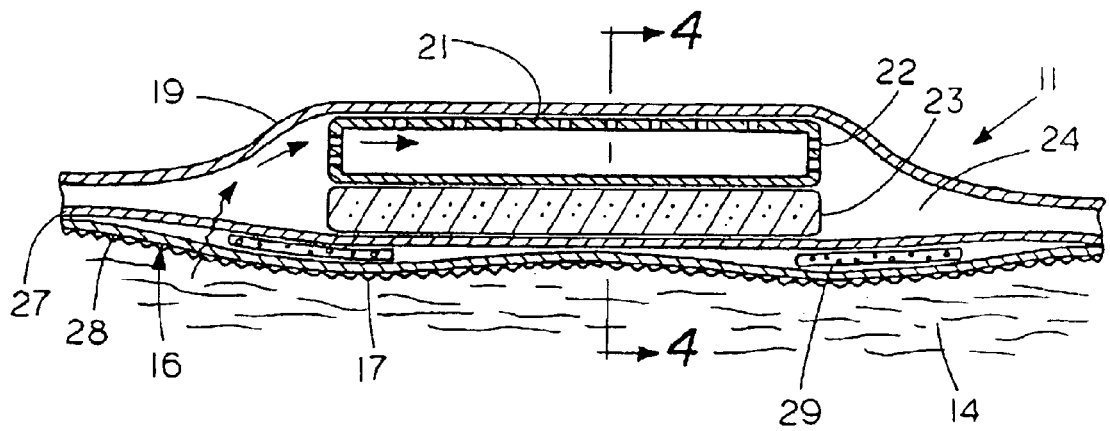

ANAEROBIC DIGESTER

CROSS REFERENCE TO RELATED APPLICATION

This application claims the benefit of U.S. provisional patent application Ser. No. 60/413,068 filed Sep. 23, 2002.

BACKGROUND OF THE INVENTION

An anaerobic digester is a device that promotes the decomposition or "digestion" of organic waste material into simple organics and gaseous biogas products. Biogas is formed by the activity of anaerobic bacteria. These bacteria occur naturally in organic environments where oxygen is limited. Biogas is a mixture of methane, carbon dioxide, hydrogen sulfide and other volatile organic compounds. It is highly corrosive due to the presence of hydrogen sulfide and water vapor. The methane gas is useful once the sulfide compounds are removed.

Anaerobic digestion in open storage vessels has historically been utilized in waste water management, especially in livestock production, to reduce or convert complex organic matter to a smaller volume. This method has proven to be economical by reducing the volume of waste handled and by volatilizing some metabolites into the atmosphere. Some disadvantages of the process include poor ability to keep the anaerobic digestion process in balance, resulting in the release of malodorous gases, and inefficient, incomplete conversion of digested organic matter into biogas. The poor quality of methane gas yielded makes the economic recovery of methane gas generally infeasible.

A passive anaerobic digester is composed of an enclosed vessel containing a slurry of organic waste material along with gas collection devices and supporting mechanical equipment. It is difficult in passive anaerobic digestion systems to consistently maintain a rate of methanogenesis that makes the recovery of the methane gas feasible. Accordingly, most passive systems flare or treat the gas collected and release it the atmosphere.

Fixed-film anaerobic digesters are those in which a media is added to the vessel to increase the surface area and give the microorganisms a surface to which they can attach. Different media have been used including plastic beads, PVC pipe, wood chips, corncobs and other media. Advantages of the fixed film vessels are high solids retention time and lower hydraulic retention time, creating a more efficient process than other designs and allowing for smaller overall vessel volume and accordingly a smaller footprint. While having satisfactory odor control characteristics, the contamination of the methane gas recovered limits its usefulness.

SUMMARY OF THE INVENTION

The invention pertains to an anaerobic digester and a method for treating organic waste and recovery from it of a usable quality methane gas. A suitable containment vessel contains a slurry of organic waste material. A first cover of gas permeable material conducive to bacterial colonization covers the surface of the waste material in the vessel. The permeable cover acts as a media to support and encourage the growth of methanogenic bacteria. This increases the efficiency of methanogenesis to more completely metabolize the malodorous short-chain volatile fatty acids resulting in a higher quality methane gas permeating the lower cover. Gas collection apparatus is installed on the first cover. A second cover of gas impermeable material is installed over the gas collection apparatus. A gas collection space is formed between the two covers. Edges of the first and second covers are closed to inhibit the escape of gas from the gas collection space. Biogas produced as a result of anaerobic digestion activity permeates the gas permeable cover and enters the collection space. From the collection space the gas is drawn into the gas collection apparatus which can, for example, be comprised of a network of perforated ducts connected to a blower that draws gas out of the ducts for delivery to a storage or usage location.

IN THE DRAWINGS

FIG. 1 is a top plan view of an embodiment of an anaerobic digester;

FIG. 2 is an enlarged sectional view of a portion of the digester of FIG. 1 taken along the line 2—2 thereof;

DESCRIPTION OF A PREFERRED EMBODIMENT

Figure 3:
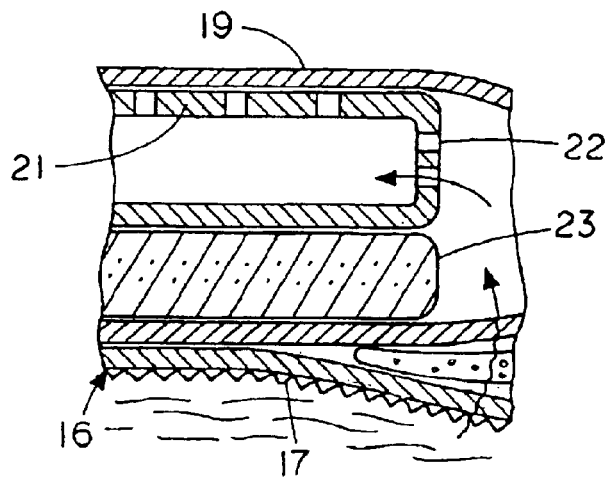
FIG. 3 is an enlarged view of a portion of the anaerobic digester shown in FIG. 2.
Figure 4:
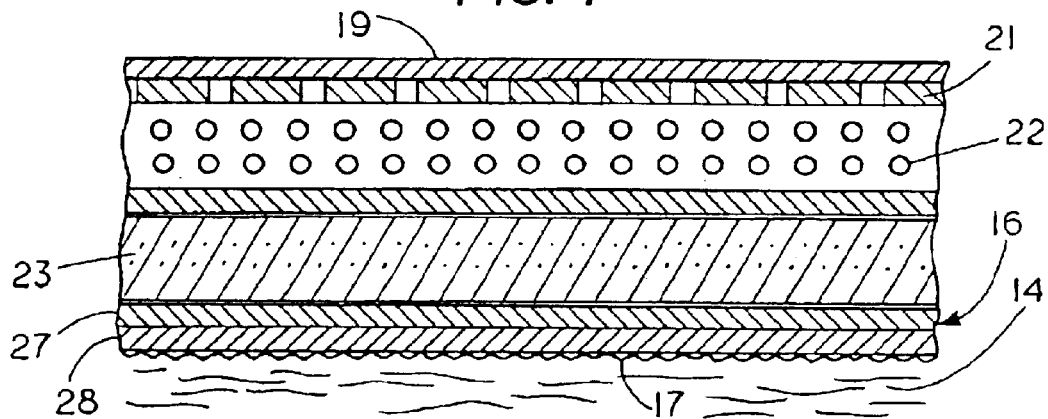
FIG. 4 is an enlarged section view of a portion of the anaerobic digester shown in FIG. 2 taken along the line 4—4 thereof.

Referring to the drawings, there is shown an anaerobic digester system 10 in FIG. 1 which includes and anaerobic digester 11 installed with respect to a containment vessel 12. Containment vessel 12 is bounded by edges 13 and is typically constructed of an earthen basin opened in the ground and lined with a suitable synthetic lining material such as a high density polyethylene. The vessel 12 contains a body of organic waste material 14 in the form of a slurry. A perimeter 15 surrounds the vessel 12.

The anaerobic digester includes a first, gas permeable cover 16 that interfaces with the organic waste material 14 and floats on top of it. Cover 16 is formed of a gas permeable material conducive to bacterial colonization that provides an environment to which methanogenic bacteria can attach and propagate in order to enhance the rate of methanogenesis within the digester system. The methanogenic bacteria form a methanogenic fixed film layer 17 on the under surface of the first cover 16. The cover 16 can be formed from a geotextile material. This is typically a polypropylene fiber, nonwoven, needle punched fabric that is stabilized to resist degradation due to ultraviolet light exposure. It typically has a specific gravity less than 1 which allows it to float like a sponge on water.

The anaerobic digester includes a duct system 18 that is installed on top of the first cover 16. A second, gas impermeable cover 19 covers the duct system 18 and the first cover 16. A gas collection space 24 is formed between the first and second covers.

The duct system 18 includes a plurality of individual pipes or ducts 21 that are parallel and span a transverse dimension of the vessel 12. Each duct 21 has a plurality of gas collection apertures or ports 22. The individual ducts 21 are connected to a main manifold or collection duct 20. Collection duct 20 is connected to a fan or blower 25 that will be typically located exterior to the vessel 13. Blower 25 is situated so as to draw gas from the main manifold 20 and discharge it through a discharge outlet 26. Gas from the discharge outlet is directed to a place of storage or use (not shown).

As shown in FIGS. 2 and 3, each individual duct 21 rests on a floatation block 23 which can be comprised of a piece of closed cell foam. The floatation block 23 rests upon the upper surface of the permeable cover 16.

First cover 16 is formed of a material conducive to the formulation and colonization of methanogenic bacteria on the lower surface thereof which form the methanogenic fixed film layer 17. Anaerobic digestion takes place in the vessel 12 and includes two distinct stages, the first being liquification or hydrolysis stage and the second being gasification. The gasification stage includes the production of short chain volatile fatty acids during acetogenesis and the production of gases such as methane, carbon dioxide, nitrogen gas and water during methanogenesis. The biogas produced moves up through the permeable cover 16. The permeable cover 16 provides an environment to which methanogenic bacteria attach and propagate. This enhances the rate of methanogenesis within the digester. Since the short chain volatile fatty acids are forced to pass through the methanogenic fixed film layer prior to entering the gas collection space 24, the greater quantity of these gases are metabolized into methane. This results in a higher quality of methane wet gas being recovered. This higher quality methane gas is more usable than other gases derived from passive anaerobic digestive systems.

The first cover 16 can be equipped with floatation in addition to any inherent floatation as a result of having a specific gravity of less than 1. In the embodiment shown, the first cover 16 has a top layer 27 and a bottom layer 28. Spaced apart foam strips 29 are disposed between the top and bottom layers 27, 28. The floatation strips 29 can be formed of a closed cell foam. Both the top and bottom layers 27, 28 can be formed of a geotextile material and can be connected by needle punching that intertwines the fibers of the two layers to connect them.

Figure 5:
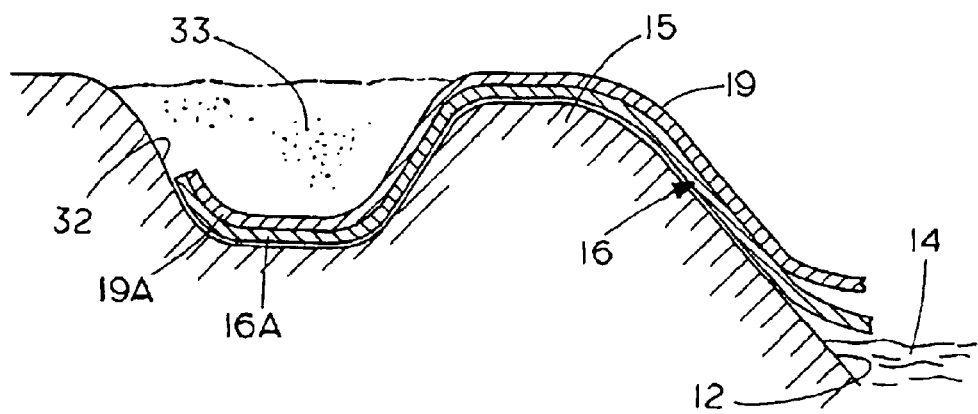
FIG. 5 is an enlarged sectional view of a portion of the anaerobic digester of FIG. 1 taken along the line 5—5 thereof.

The edges of the second cover 19 and the first cover 16 are closed in order to inhibit the loss of gas entrapped between them. The edges of the covers extend beyond the edges 13 of the vessel 12 and over the perimeter 15 surrounding the vessel 12. One means of closing the edges is illustrated in FIG. 5. A trench 32 is formed in the perimeter 15 surrounding the vessel 12. The edges 16A, 19A of the first and second covers 16, 19 are positioned in the trench 32. Trench 32 is then filled with a suitable fill material such as a quantity of dirt 33.

In use, anaerobic digestion takes place in the organic slurry 14 contained in the vessel 12. The anaerobic digester substantially covers the entire surface of the vessel 12 and floats on top of the organic waste material 14. Biogas produced by anaerobic digestion taking place in the organic material passes through the permeable cover 16. In doing so it passes through the methanogenic film layer that has formed on the under surface of the permeable cover 16. An improved quality of methane gas enters into the collection space 24 between the first and second covers 16, 19. The gas passes through the ports 22 into the interior of the ducts 21. Blower 25 operates to draw the gas through the ducts 21 and the manifold 20 and out the discharge 26. Discharge 26 is connected to a suitable storage reservoir, or directly to an end use appliance.

While one embodiment has been shown and described herein, it will be apparent to those skilled in the art that deviations can be made from the embodiment shown herein without departing from the scope and spirit of the attached claims.

The embodiments of the invention in which an exclusive property or privilege is claimed are defined as follows:

1. An anaerobic digester for installation on an upwardly open containment vessel containing a body of organic waste material slurry comprising:
   a first cover made of gas permeable material conducive to bacterial colonization for installation on the surface of a body of organic waste material slurry in a containment vessel;
   at least one gas conveying duct installed on the top of the first cover when the first cover is installed on the surface of a body of organic waste material;
   a second cover made of gas impermeable material installed over the first cover and over the gas conveying duct forming a gas collection space with the first cover;
   the first and second covers having edges that are closed together in order to inhibit the escape of gas from between them;
   said duct having a plurality of ports for passage of gas from the gas collection space into the duct;
   blower means connected to the duct to move gas out of the duct to a remote location for storage or use.

2. The anaerobic digester of claim 1 including:
   a plurality of interconnected gas collection ducts spaced apart on the surface of the first cover and connected to the blower means.

3. The anaerobic digester of claim 1 including:
   a plurality of interconnected gas collection ducts arranged in parallel relationship on the surface of the first cover.

4. The anaerobic digester of claim 3 including:
   a main manifold connected to the ducts and to the blower means.

5. The anaerobic digester of claim 3 wherein:
   the edges of the first and second covers are closed together by placing the edges together in a trench bounding the containment vessel and filling the trench with a fill material.

6. The anaerobic digester of claim 3 including:
   flotation blocks supporting the gas conveying ducts on the surface of the first cover.

7. The anaerobic digester of claim 6 including:
   flotation panels connected to the first cover.

8. The anaerobic digester of claim 7 wherein:
   said first cover is made from a geotextile material.

9. The anaerobic digester of claim 8 wherein:
   said first cover includes a first layer and a second layer with said flotation panels disposed between the first and second layers.

10. The anaerobic digester of claim 3 wherein:
    said first cover floats.

11. The anaerobic digester of claim 10 including:
    flotation blocks supporting the gas conveying ducts on the surface of the first cover.

12. The anaerobic digester of claim 10 wherein:
    said first cover includes a first layer and a second layer, and including flotation panels disposed between the first and second layers.

13. An anaerobic digester system for recovery of a usable grade of methane gas from organic waste material slurry, comprising:
    an upwardly open containment vessel for containment of organic waste material slurry;
    a first cover made of gas permeable material conducive to bacterial colonization for installation on the surface of a body of organic waste material slurry in the containment vessel;

a gas collection system installed on the top of the first cover when the first cover is installed on the surface of a body of organic waste material;

a second cover made of gas impermeable material installed over the first cover and over the gas collection system forming a gas collection space with the first cover;

the first and second covers having edges that are closed together in order to inhibit the escape of gas from between them;

blower means connected to the gas collection system to move gas out of gas collection space to a remote location for storage or use.

14. The anaerobic digester system of claim 13 wherein:

said gas collection system includes a plurality of interconnected gas collection ducts spaced apart on the surface of the first cover and connected to the blower means.

15. The anaerobic digester system of claim 13 wherein:

said gas collection system includes a plurality of interconnected gas collection ducts arranged in parallel relationship on the surface of the first cover.

16. The anaerobic digester system of claim 15 including:

a main manifold connected to the ducts and to the blower means.

17. The anaerobic digester system of claim 15 wherein:

the edges of the first and second covers are closed together by placing the edges together in a trench bounding the containment vessel and filling the trench with a fill material.

18. The anaerobic digester system of claim 15 including:

flotation blocks supporting the gas conveying ducts on the surface of the first cover.

19. The anaerobic digester system of claim 18 including:

flotation panels connected to the first cover.

20. The anaerobic digester system of claim 18 wherein:

said first cover is made from a geotextile material.

21. The anaerobic digester system of claim 20 wherein:

said first cover includes a first layer and a second layer with said flotation panels disposed between the first and second layers.

22. The anaerobic digester system of claim 15 wherein:

said first cover floats.

23. The anaerobic digester system of claim 22 including:

flotation blocks supporting the gas conveying ducts on the surface of the first cover.

24. The anaerobic digester system of claim 22 wherein:

said first cover includes a first layer and a second layer, and including flotation panels disposed between the first and second layers.

25. A method of recovering a usable grade of methane gas from a body of organic waste material in slurry form, comprising:

covering the surface of the slurry with an anaerobic digester having a first cover made of a gas permeable material conducive to bacterial colonization, a second cover of gas impermeable material having edges closed to the edges of the first cover forming a gas collection space between the first and second covers, a gas collection duct with gas passage apertures located in the gas collection space so that gas from the slurry permeates the first cover and enters the space between the first and second covers; and drawing off through the duct the gas collected in the gas collection space between the first and second covers.

26. The method of claim 25 including:

using a blower to draw the gas through the duct.

27. A method of recovering a usable grade of methane gas from a body of organic waste material in slurry form, comprising:

covering the surface of the slurry with a first cover of gas permeable material conducive to bacterial colonization;

installing a gas collection duct having a plurality of gas collection apertures on the first cover;

installing a second cover of gas impermeable material over the first cover and the gas collection duct with edges of the second cover closed to edges of the first cover to form a gas collection space between the first and second covers;

drawing off through the gas collection duct gas which enters the gas collection space from the slurry through the first cover.

28. The method of claim 27 including:

using a blower to draw the gas from the gas collection duct.

* * * * *